(12) United States Patent
Auld et al.

(10) Patent No.: US 9,877,445 B2
(45) Date of Patent: Jan. 30, 2018

(54) USE OF THE NAKED-TUFTED MUTANT IN UPLAND COTTON TO IMPROVE FIBER QUALITY, INCREASE SEED OIL CONTENT, INCREASE GINNING EFFICIENCY, AND REDUCE THE COST OF DELINTING

(75) Inventors: Dick L. Auld, Lubbock, TX (US); Efrem Bechere, Lubbock, TX (US)

(73) Assignee: Texas Tech University System, Lubbock, TX (US)

( * ) Notice: Subject to any disclaimer, the term of this patent is extended or adjusted under 35 U.S.C. 154(b) by 1103 days.

(21) Appl. No.: 12/197,296

(22) Filed: Aug. 24, 2008

(65) Prior Publication Data

US 2009/0055962 A1 Feb. 26, 2009

Related U.S. Application Data

(60) Provisional application No. 60/957,958, filed on Aug. 24, 2007.

(51) Int. Cl.
*A01H 5/10* (2006.01)
(52) U.S. Cl.
CPC ...................................... *A01H 5/10* (2013.01)
(58) Field of Classification Search
CPC ................................... A01H 5/00; A01H 5/10
USPC .......................................................... 800/314
See application file for complete search history.

(56) References Cited

PUBLICATIONS

Bechere et al. 2009. Euphytica 167:333-339.*
Poehlman and Sleper. 1995. Mutation, Chapter 6, pp. 106-115, In Breeding Field Cros, 4th edition.*
Endrizzi et al. 1991. J. Heredity 82: 53-57.*
Poehlman and Sleper (Mutation, Chapter 6, pp. 106-115, In Breeding Field Crops, 4th edition, 1995).*
Endrizzi and Ray (J. Heredity 82: 53-57, 1991).*
Bechere et al (Euphytica 167: 333-339, 2009).*
Endrizzi and Ray. J. Heredity 82: 53-57, 1991.*
Poehlman and Sleper. Mutation, Chapter 6, pp. 106-115, In Breeding Field Crops, 4th edition, 1995.*
Bowman, D.T. et al., "Genetic Base of Upland Cotton Cultivars Released Between 1970 and 1990", Crop Science, vol. 36, pp. 577-581, 1996.
Herring, Andy D. et al., "Inheritance of Fiber Quality and Lint Yield in a Chemically Mutated Population of Cotton", Euphytica 136. pp. 333-339, 2004, Netherlands.
Auld, D.L. et al., "Chemical Mutagenesis as a Tool in Cotton Development", Proc. Beltwide Cotton Prod. Res. Conf., Memphis, TN, vol. 1, pp. 550-552, 1998.
Auld, D.L. et al, "Registration of TTU 202-1107-B and TTU 271-2155-C Mutant Germplasm Lines . . . Improved Fiber Quality", Crop Science, vol. 40, pp. 1835-1836, 2000.
Key, C.A. et al., "Selection of Stovepipe Lines from Chemically Mutated Cotton", Proc. Beltwide Cotton Prod. Res. Conf., Memphis, TN, vol. 1, pp. 492-493, 1998.
Auld, D.L. et al., "Inheritance of Fiber Length in Two Mutants of Cotton", Proc. Beltwide Cotton Prod. Res. Conf., Memphis, TN, vol. 1, pp. 518-520, 2000.
Auld, D.L. et al, "Rapeseed Mutants with Reduced Levels of Polyunsaturated Fatty Acids and Increased Levels of Oleic Acid", Crop Science, vol. 32, pp. 657-662, 1992.
Salanki, et al,.Colchicine-Induced Mutant in Cotton (*Gossypium Hirsutum*, L), Current Science, vol. 12, pp. 356-357, 1968.
Kearney, Thomas H. et al., "Inheritance of Smooth Seeds in Cotton", Journal of Agricultural Research, vol. 35, No. 3, pp. 193-217, 1927.
Basal, H. et al., "The Association of Fiber Quality . . . Upland Cotton Populations", Proc. Beltwide Cotton Conf., Memphis, TN, vol. 1, pp. 478-479, 1997.
Cantrell, R.G. et al., "Genetics of Fiber Strength", Proc. Beltwide Cotton Prod. Res. Conf, Memphis, TN, vol. 2, p. 1627, 1997.
Gibson, P.T., "Correcting for Inbreeding in Parent-Offspring Regression . . . Effects Present", Crop Science, vol. 36, pp. 594-600, 1996.
Green, C.C. et al., "The Inheritance and Relationship of Yield and . . . Breeding Program", Proc. Beltwide Cotton Prod. Conf., Memphis, TN, vol. 1, p. 131, 1988.
Keim, K. R. et al., Inheritance of Fiber Quality . . . Composite of Cotton (*Gossypium hirsutum* L.), Proc. Beltwide Prod. Res. Conf., Memphis, TN, vol. 1, p. 108, 1983.
Kloth, R.H, "Analysis of Commonality for Traits of Cotton Fiber", J. Cotton Sci., vol. 2, pp. 17-22, 1998.
Konoplya, S.P. et al., "Heritability of Several Quantitative Characters in Cotton", Soviet Genetics vol. 10, pp. 1462-1464, 1974.
Latimer, S. L. et al, "Cotton Breeding: High Volume Instrument . . . Quality Testing", Proc. Beltwide Cotton Prod. Res. Conf., Memphis, TN, vol. 3, p. 1681, 1996.
May, O. L. et al., "Genetic Modification of Cotton Fiber . . . High Volume Instruments", Crop Science, vol. 39, pp. 326-333, 1999.
Meredith, W. R., Jr., "Quantitative Genetics", Cotton Agronomy Monograph No. 24, ASA, CSSA, and SSSA, Madison, WI, pp. 131-150, 1984.
Naivar, K.S., Fiber Quality Parameters and . . . Gossypium arboreum:, Putative Mutant Lines, M.S. Thesis, Texas A&M Univ., pp. 1-71, 1996.
Du, X. M. et al., "Genetic Analysis of Presence and Absence of Lint and Fuzz in Cotton", Plant Breeding, vol. 120, pp. 519-522, 2001.
Endrizzi, J. E. et al., "Monosomic and Monotelodisomic . . . Loci in Cotton", Journal of Heredity, vol. 82, pp. 53-57, 1991.

(Continued)

*Primary Examiner* — Keith O Robinson
(74) *Attorney, Agent, or Firm* — Edwin S. Flores; Daniel J. Chalker; Chalker Flores, LLP (57) ABSTRACT

Described is a naked-tufted seed mutant line of *Gossypium hirsutum* L., developed from lines initially produced by chemical mutagenesis, which significantly reduces the formation of linters on the surface of the cotton seed. In a preferred embodiment, the lines carrying the naked seed mutation have reduced seed coat neps, reduced short fiber content, improved yarn quality, increased seed oil content, and improved AFIS fiber maturity. The naked-tufted seed of the mutant line significantly reduces the time and energy required for ginning, oil extraction, and reduces the need to delint the cotton seed prior to planting. In a preferred embodiment, the mutant is incorporated into a well-adapted commercial cultivar of upland cotton.

10 Claims, 2 Drawing Sheets

(56) References Cited

PUBLICATIONS

Lee, J. J. et al., "Developmental and Gene Expression Analyses of a Cotton Naked Seed Mutant", Planta vol. 223, pp. 418-432, 2006.
Turley, R. B. et al., "Identification of a Thord Fuzzless Seed Locus in Upland Cotton (*Gossypium hirsutum* L.)", Journal of Heredity, vol. 93, No. 5, pp. 359-364, 2002.
Gaibullaev, I. K. H. et al., "Reaction of Chemomutants of Cotton to Infection . . . Verticillium Wilt", Soviet Genetics, vol. 11, No. 1, pp. 34-36, 1976.
Hussein, H.A.S. et al., "Histological and Morphological Characteristics of . . . Sodium Azide", Egypt J. Genetics, vol. 11, pp. 167-173, 1982.
Larik, A. S. et al., Azide Mutagenesis in Cotton (Gossypium hirsutum), Science and Environment, vol. 5, pp. 33-42, 1983.
Shattuck, V. et al., "Enhanced Unscheduled DNA Synthesis . . . Methanesuifonate (EMS)", Biochemical and Biophysical Research Communications, vol. 109(3), pp. 1017-1025, 1982.
Van Winkle, K., "USA Cotton Quality Measurements and Analysis", Cotton Inc., 2000 Upland Crop Final Report, pp. 1-25, Apr. 20, 2001.

\* cited by examiner

Fig. 1

Fig. 2D  Fig. 2C  Fig. 2B  Fig. 2A

USE OF THE NAKED-TUFTED MUTANT IN UPLAND COTTON TO IMPROVE FIBER QUALITY, INCREASE SEED OIL CONTENT, INCREASE GINNING EFFICIENCY, AND REDUCE THE COST OF DELINTING

CROSS REFERENCE TO RELATED APPLICATION

This application claims the benefit under Title 35 United States Code § 119(e) of U.S. Provisional Application No. 60/957,958; Filed: Aug. 24, 2007, the full disclosure of which is incorporated herein by reference.

FIELD OF THE INVENTION

The present invention relates generally to cotton cultivars, methods for producing the cultivars, and products obtained from the cultivars. The present invention relates more specifically to novel mutants, and methods for developing mutant lines, in upland cotton and their incorporation into an appropriate commercial cultivar in order to develop cultivars having "quality enhancing traits" without deleterious side effects.

DEPOSIT OF BIOLOGICAL MATERIAL

The following biological material has been deposited under the terms of the Budapest Treaty with the National Laboratory for Genetic Resources Preservation, 1111 S. Mason Street, Fort Collins, Colo., USA, and given the following number:

| Deposit | Accession Number | Date of Deposit |
|---|---|---|
| $M_{6:7}$ seeds *Gossypium hirsutum* L. | P1667553 | Dec. 8, 2017 |

The seeds have been deposited under conditions that assure that access to the seeds will be available during the pendency of this patent application to one determined by the Commissioner of Patents and Trademarks to be entitled thereto under 37 C.F.R. § 1.14 and 35 U.S.C. § 122. The deposit represents Tufted-Naked Seed Upland Cotton Germplasm. The deposit is available as required by foreign patent laws in countries wherein counterparts of the subject application, or its progeny are filed. However, it should be understood that the availability of a deposit does not constitute a license to practice the subject invention in derogation of patent rights granted by government action.

BACKGROUND OF THE INVENTION

Cotton is the world's leading textile fiber and it is grown on over six million hectares in the United States (US) (USDA-National Agricultural Statistics Service, 2005). Cotton is one of the leading cash crops in the U.S. Cotton fiber generates in excess of $6 billion per year, while cottonseed oil and meal add another $500 million per year to the total US agricultural economy. More than 440,000 domestic jobs are created by cotton production and processing which has a total impact of over $40 billion on the US gross domestic product (National Cotton Council 2005). U.S. cotton exports also contribute about $2 billion per year to our trade balance.

Cotton has been selected and cultivated primarily for its fiber. Although the seed now is used in the production of oil, meal, and dairy feed, its economic value to the modern farmer for these uses is low in comparison to the economic value of the fiber, which is used to produce yarn, fabric and textile garments. Despite the greater mass per acre of seed as compared to fiber, the even greater economic value per pound of fiber as compared to seed has encouraged plant breeders to select cotton primarily for increased fiber yield and fiber quality, and only secondarily for increased seed yield and seed quality. As a result of this intense selection for genetic improvements in fiber yield, the genetic contribution to fiber yield and lint percent has increased during the last 50 years while seed size has declined.

The 1.3 billion pounds of cottonseed oil produced each year make it the third leading vegetable oil in the U.S. The cottonseed industry is a $1.2 billion industry and has historically provided up to 15% of the gross return on cotton production. Thus, there is a need to increase the yield of cottonseed oil as well as cotton fiber yield and fiber quality, while simultaneously reducing the cost of producing these commercially important products.

Nearly 20% of the U.S. total cotton production (three million bales) occurs on the High Plains of Texas. Because of the relatively poor fiber quality of the cultivars adapted to this short growing season region, this cotton has historically been sold to low value markets. Currently, there is a need to improve cotton fiber quality and seed oil content and to reduce the cost of production for the cotton cultivars adapted to this region. Studies have been conducted to determine the inheritance of improvements in fiber quality in cotton. There is a need to develop cotton seed mutants which have the potential to improve fiber quality without introducing alien genes that may reduce adaptation to production regions having a short growing season.

Ideally, the incorporation of such traits into well-adapted commercial cultivars would speed up and reduce the cost of ginning, reduce the need for delinting cotton seed used for planting, increase seed oil content, reduce the need to remove linters prior to oil extraction, and improve cotton fiber quality by reducing seed coat neps and short fiber content, thus maximizing the economic value and commercial utility of cotton crops.

The use of chemically-induced mutants has been highly successful in most major crops grown across the world but has only occasionally been used in improving cotton (Auld et al., 1998). However, the relatively low level of genetic variability currently available in cotton would indicate this would be an ideal tool to increase genetic variability in this species. Mutagenesis has been shown to be an effective tool to create a wide range of phenotypic variation in both diploid and tetraploid *Gossypium* populations (Auld et al., 2000; Larik et al., 1983; Gaibullaev et al., 1976; Hussein et al., 1982 and Shattuck and Katterman, 1982). The creation of these new mutants is a powerful tool for both functional genetics and conventional genetic improvement of cotton.

The cotton cultivars adapted to the High Plains of Texas, unlike commercial upland cotton, have a narrow germplasm base that has limited the success of breeding programs attempting to improve fiber quality using conventional breeding techniques. Recent studies at Texas Tech University indicate successful mutagenesis in cotton from exposure of germinating embryos to high rates of ethyl methanesulfonate (EMS). These studies of mutant lines reveal significant potential for improvement of fiber quality in cotton. Such developmental studies using chemical mutagenesis for inducing heritable variation in cotton fiber quality show promise for cotton markets where fiber quality is at a premium.

SUMMARY OF THE INVENTION

It is therefore an object of the present invention to provide a novel mutant in upland cotton combining improved fiber quality with increased seed oil content.

It is also an object of the present invention to provide a novel mutant in upland cotton which is easily distinguishable on the basis of naked-tufted seed coat from other cotton seeds.

It is another object of the present invention to incorporate a novel mutant in upland cotton into an appropriate commercial cultivar in order to develop cultivars that consistently express characteristics of improved fiber quality, increased seed oil content, and reduced production costs to significantly reduce both the time and the energy required for ginning, oil extraction, and delinting of cottonseed.

It is a further object of the present invention to provide novel cotton plants that can be used efficiently to produce parent lines possessing desirable agronomic traits.

It is yet another object of the present invention to provide a method for producing a novel cotton plant that has seed which has reduced seed coat neps and potentially reduced short fiber content.

It is still another object of the present invention to provide a *Gossypium hirsutum* L. seed product of a substantially homogeneous assemblage of cotton seeds which has reduced seed coat neps, reduced short fiber content, and/or increased oil content.

In accomplishing the foregoing objects, there has been provided, in accordance with the present invention, a naked-tufted seed mutant of *Gossypium hirsutum* L., from lines initially produced by chemical mutagenesis, which significantly reduces the formation of linters on the surface of the cotton seed and does not have an excessive yield penalty, i.e., reduction in lint yield and percent lint.

In a preferred embodiment, the lines carrying the naked seed mutation have reduced seed coat neps, reduced short fiber content, improved yarn quality, and improved AFIS fiber maturity characteristics. There has also been provided in accordance with the present invention a mutant cotton seed which significantly reduces the time and energy required for ginning, oil extraction, and reduced need to acid delint cotton seed prior to planting. In a preferred embodiment, this naked-tufted seed mutant is incorporated into a well-adapted commercial cultivar of upland cotton to enhance crop quality and reduce processing costs.

DETAILED DESCRIPTION OF THE PREFERRED EMBODIMENTS

The narrow germplasm base of the upland cotton (*Gossypium hirsutum* L.), historically grown on the Texas high plains, has limited the improvement of fiber quality. Chemical mutagenesis and subsequent selection have helped the development of lines with improved fiber quality in cultivars adapted to this region. Based upon these developmental studies for inducing heritable variation in fiber quality, the present invention discloses a "naked seed mutant" which significantly reduces the formation of linters on the surface of the cottonseed. This mutant has been shown to significantly enhance oil content in cottonseed ($r=0.68^{*}$). The naked seed mutant also has a profound impact on lint quality. The lines carrying the naked seed mutation have reduced seed coat neps ($r=-0.47^{*}$), potentially reduced short fiber content, improved yarn quality and improved AFIS fiber maturity. These are the factors which have prevented successful development of ELS (Extra Long Staple) stripper varieties in Texas. This naked seed mutation can also significantly reduce both the time and energy required for ginning, oil extraction, and delinting of cottonseed. The present invention therefore provides characterization of naked-tufted seed coat mutants with respect to oil content, lint yield, lint percent, fiber quality, and yarn spinning performance.

Figure 1:
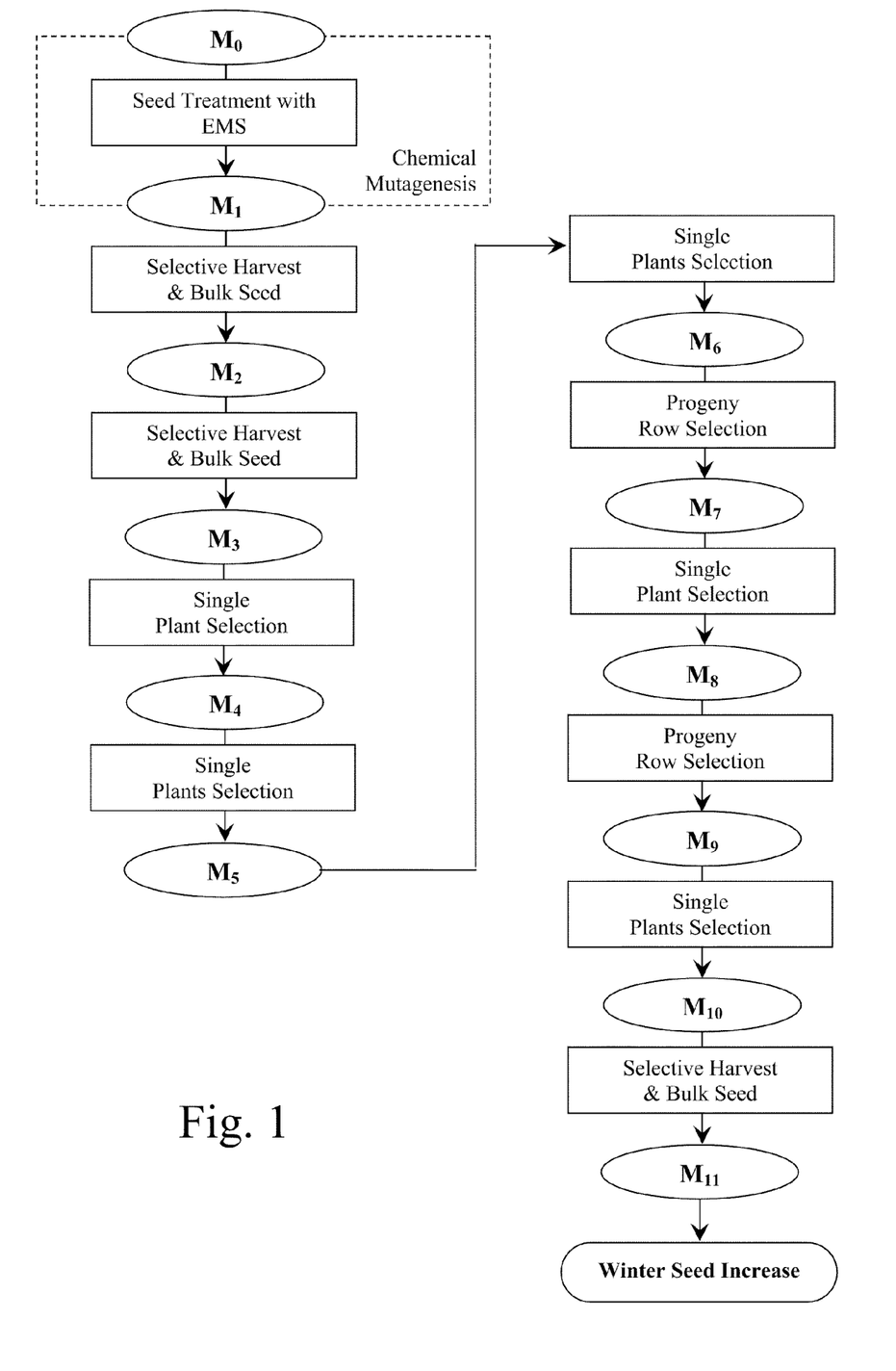
FIG. 1 is a schematic diagram outlining the development of the mutant lines established according to the methods of the present invention.
Figure 2A:
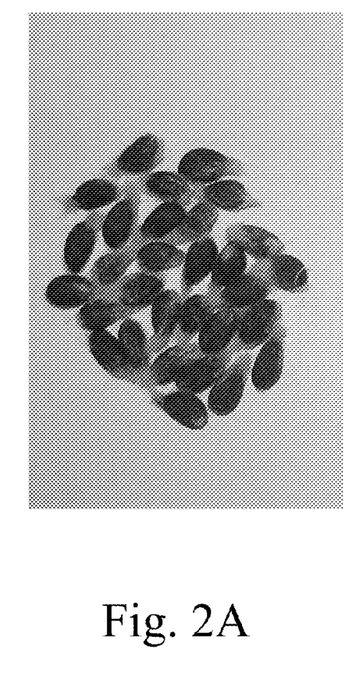
FIGS. 2A-2D are photo images of sample assemblages of seeds of four cotton lines demonstrating differential expression of the "naked and tufted" phenotype after saw ginning: (A) naked seed; (B) partially naked seed; (C) partially fuzzy seed; and (D) fuzzy seed.
Figure 2B:
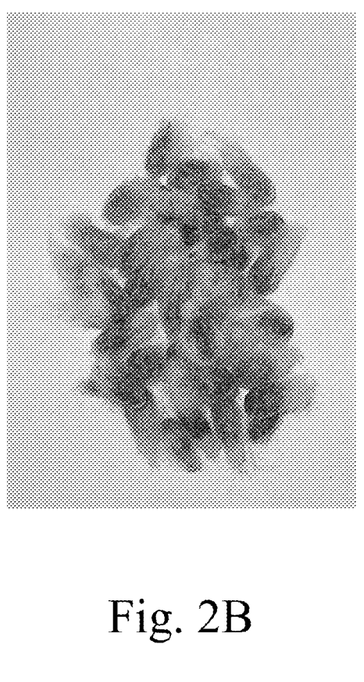
Figure 2C:
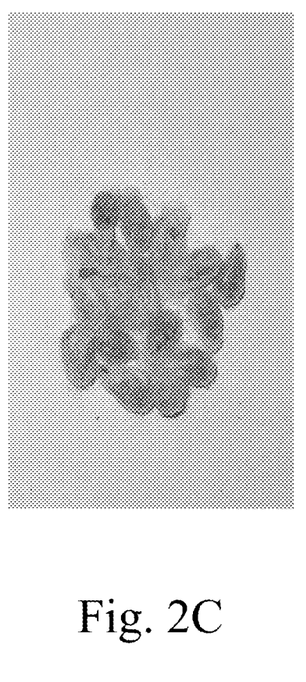
Figure 2D:
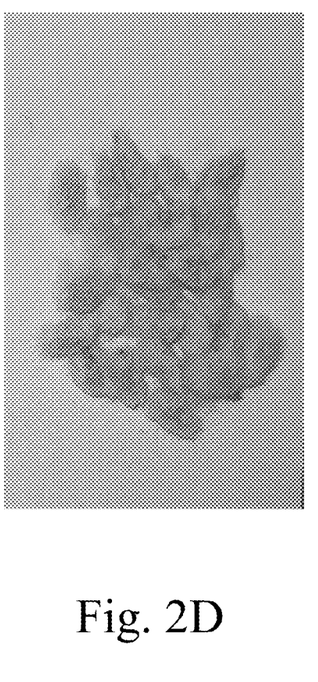

FIG. 1 provides a schematic outline of the development of the naked-tufted mutant lines established according to the present invention. In 1996, six commercial varieties of cotton were treated with 2.45% v/v ethyl methanesulfonate (EMS). In 1999, three $M_3$ plants were identified that had partially naked (naked-tufted) seed coats. FIGS. 2A-2D show sample assemblages of seeds of four cotton lines demonstrating differential expression of the "naked and tufted" phenotype after saw ginning: (A) naked seed; (B) partially naked seed; (C) partially fuzzy seed; and (D) fuzzy seed. From 2001 to 2004, selections from the three $M_3$ naked-tufted seed coat mutants were evaluated in replicated trials. These trials were conducted to stabilize this trait and to evaluate the impact of the naked-tufted phenotype on lint yield, lint percent, fiber quality, and yarn spinning performance. In 2001, the initial three mutants were visually screened for the expression of naked-tufted seed coats. Fifteen individual plants exhibiting the naked-tufted phenotype were selected and grown in the field in 2002. This process was repeated in 2003 and 2004 to generate 40 individual plant selections with naked-tufted seed coats. In 2005 and 2006, these 40 selections ($M_7$ lines), three parental lines and five check cultivars of cotton (*Gossypium hirsutum* L.) were evaluated for expression of the naked-tufted seed coat trait, lint yield and lint percent. The fibers harvested from these plots were analyzed at Texas Tech University using High Volume Instruments (HVI), Advanced Fiber Information Systems (AFIS), and standard yarn quality analyses.

These naked-tufted mutants appear to significantly reduce the occurrence of fuzz or linters (short fibers tightly attached to the seed coat in most upland cotton varieties). These mutants appear to be phenotypically similar to the "naked-tufted" mutant initially described by Endrizzi and Ray in 1991 (concluding that the $N^t_2$ marker was a simple dominant gene, allelic to $n_2$, and located on the long arm of chromosome 26). Initial interest in these phenotypes was based on the hypothesis that the removal of linters during saw ginning contributed significantly to increased short fiber content in upland cotton. Consequently, genetic elimination of the linters would reduce the short fiber content while simplifying ginning, oil recovery, and delinting of cottonseed.

Turley and Kloth had earlier reported on the impact of the $N_1/n_1$, $N_2/n_2$, and the $N_3/n_3$ genes on lint percent in cotton (Turley and Kloth, 2002). They proposed that only the genotype, $n_1n_1N_2N_2N_3N_3$, would generate a normal lint percent of 40.5%. A second study by Lee et al., reported on the gene expression of the $N_1N_1$ genotype and its impact on fuzz development (Lee et al. 2006). Neither of these studies, however, included analyses of the $N^t_2$ allele or an estimate of its impact on lint percent.

Based on data collected on 2005 and 2006 fiber, it appeared that a selected line with a partially naked seed coat (SC 9023-NS-57-13-3) did have reduced short fiber content, enhanced maturity, and higher quality yarn that provided exceptional performance for ring spinning applications. However, not all partially naked or naked seed coat lines show similar performance, indicating that other factors in addition to seed coat characteristic impart short fiber content and fiber maturity. Detailed analyses of the data during 2005 and 2006 showed that the five naked-tufted seed mutant lines evaluated had lint percent (turn out) that ranged from 37 to 43% compared to 39 to 43% for the normal fuzzy parental check varieties. HVI analyses did not identify this line as superior, but AFIS analyses showed that fibers produced on the naked-tufted genotypes consistently had smaller neps (Nepsize), fewer seed coat neps (SCNCnt), and often a reduced percent of short fibers (SFCn). The naked-tufted phenotype was correlated with a reduction in seed coat neps (r=−0.47) and an increase in seed oil content (r=0.68). The present invention reveals that selected naked-tufted mutants have comparable lint yields and lint percent of both the parental cultivars and commercial check cultivars. Several of the mutants also have very good HVI and AFIS fiber quality. The tables below provide summaries of some of the more recent research data and analysis for the naked seed mutants indicating the further establishment of the above described results.

Table 1 reveals the lint yield, percent lint, and seed nakedness for selected naked seed mutants, their original parents, and two check varieties. This comparative data indicates that the incorporation of the naked-tufted seed coat trait does not significantly alter the lint yield or turnout of the mutant lines when compared to their original parents.

TABLE 1

Lint Yield, Percent Lint and Seed Nakedness for Some Naked Seed Mutants, Their Original Parents and Two Check Varieties

| Entry | Lint Yield | | | Turnout | | | | | Seed Nakedness % |
|---|---|---|---|---|---|---|---|---|---|
| | 2006 | 2007 | Mean | 2006 (LBB) | 2007 (LBB)[1] | 2007 (LBB)[2] | 2007 (Col. St) | Mean | |
| | lbs/acre | | | % | | | | | |
| Atlas | 1369 | 1583 | 1476 | 40 | 39 | 44 | 37 | 40 | 0.00 |
| Atlas-NS-129-2-1-1-1 | 1189 | 1524 | 1357 | 38 | 41 | 41 | 33 | 38 | 0.36 |
| SC 9023 | 1346 | 1473 | 1410 | 40 | 37 | 40 | 36 | 38 | 0.00 |
| SC 9023-NS-57-13-2-1 | 1374 | 1240 | 1307 | 39 | 37 | 39 | 34 | 37 | 0.37 |
| Tejas | 1334 | 1530 | 1432 | 41 | 39 | 42 | 37 | 40 | 0.00 |
| Tejas-NS-28-13-3-1-1 | 1207 | 1393 | 1300 | 43 | 39 | 40 | 37 | 40 | 0.36 |
| FM 989 | 1255 | — | 1255 | 43 | — | 44 | — | 44 | 0.00 |
| FM 958 | 1481 | — | 1481 | 43 | — | 47 | 41 | 44 | 0.00 |
| CV (%) | 10.8 | 12 | | 4.8 | 5.3 | 4.6 | 5.0 | | 8.1 |
| LSD (0.05) | 202 | 265 | | 2.0 | 3.4 | 3.4 | 8.4 | | 0.05 |

Table 2 reveals the oil content and fatty acid composition for selected naked seed mutants, their original parents, and check varieties. This comparative data indicates that the incorporation of the naked-tufted seed coat trait generally increases seed oil content in the mutant lines when compared to their original parents.

TABLE 2

Oil Content and Fatty Acid Composition for Some Naked Seed Mutants, Their Original Parents and Check Varieties.

| Entry | Oil Content | | | Fatty Acid Composition* | | | |
|---|---|---|---|---|---|---|---|
| | 2006 | 2007 | Mean | Palmitic (16:0) | Stearic (18:0) | Oleic (18:1) | Linoleic (18:2) |
| | % | | | | | | |
| Atlas | 15.4 | 20.1 | 17.8 | 24.5 | 2.7 | 19.6 | 49.6 |
| Atlas-NS-129-2-1-1-1 | 17.4 | 20.3 | 18.9 | 22.5 | 2.8 | 19.3 | 54.3 |
| SC 9023 | 14.8 | 18.4 | 16.6 | 25 | 2.7 | 17.4 | 51.5 |
| SC 9023-NS-57-13-2-1 | 17.1 | 21.1 | 19.1 | 21.1 | 2.8 | 19.3 | 53.2 |
| Tejas | 15.9 | 20.7 | 18.3 | 23.6 | 2.7 | 19.8 | 50.8 |
| Tejas-NS-28-13-3-1-1 | 16.9 | 19.9 | 18.4 | 24.1 | 2.9 | 18.1 | 51.7 |
| FM 989 | 15.7 | 20.7 | 18.2 | 24 | 2.7 | 17.4 | 52.8 |
| FM 958 | 15.8 | 20.5 | 18.2 | 24.9 | 2.7 | 18.7 | 50.5 |

TABLE 2-continued

Oil Content and Fatty Acid Composition for Some Naked Seed Mutants, Their Original Parents and Check Varieties.

| | Oil Content | | | Fatty Acid Composition* | | | |
|---|---|---|---|---|---|---|---|
| Entry | 2006 | 2007 % | Mean | Palmitic (16:0) | Stearic (18:0) | Oleic (18:1) | Linoleic (18:2) |
| CV (%) | 2.4 | 5.2 | | 4.8 | 6.5 | 5.6 | 2.5 |
| LSD (0.05) | 0.84 | 1.8 | | 2.2 | 0.4 | 2.1 | 2.7 |

*Normal cotton on the average has 22% Palmitic, 15% Oleic, 49% Linoleic, and 2.7% Stearic Table 3 reveals the lint per seed, fiber per seed, and fiber per mm$^2$ for selected naked seed mutants, their original parents, and check varieties. This comparative data indicates that the incorporation of the naked-tufted seed coat trait generally reduces the lint per seed and the fiber per seed for the mutant lines when compared to their original parents. This data supports the commercial viability of cotton products from the mutant lines.

TABLE 3

Lint per seed, Fiber per seed, and Fiber per mm$^2$ for some naked seed Mutants, their original parents and check varieties.

| | Lint per seed | | | Fiber per seed | | | Fiber per mm$^2$ | | |
|---|---|---|---|---|---|---|---|---|---|
| Entry | 2006 | 2007 (mg) | Mean | 2006 | 2007 (no.) | Mean | 2006 | 2007 (no.) | Mean |
| Atlas | 68.6 | 70.3 | 69.5 | 17767 | 19462 | 18615 | 181 | 192 | 187 |
| Atlas-NS-129-2-1-1-1 | 57.0 | 63.3 | 60.2 | 15206 | 19888 | 17547 | 157 | 206 | 182 |
| SC 9023 | 66.9 | 65.7 | 66.3 | 17013 | 17706 | 17360 | 173 | 168 | 171 |
| SC 9023-NS-57-13-2-1 | 59.3 | 56.7 | 58.0 | 15652 | 16416 | 16034 | 161 | 165 | 163 |
| Tejas | 69.4 | 74.7 | 72.1 | 18636 | 20989 | 19813 | 194 | 193 | 194 |
| Tejas-NS-28-13-3-1-1 | 72.8 | 75.3 | 74.1 | 18893 | 20032 | 19463 | 181 | 177 | 179 |
| FM 989 | 76.2 | 78 | 77.1 | 19834 | 19920 | 19877 | 210 | 201 | 206 |
| FM 958 | 77.6 | 87 | 82.3 | 19223 | 21432 | 20328 | 196 | 209 | 203 |
| CV (%) | 7.0 | 6.5 | | 7.2 | 10.0 | | 7.2 | 9.7 | |
| LSD (0.05) | 3.8 | 8.2 | | 1019 | 3420 | | 10.3 | 32.0 | |

Table 4a reveals AFIS Data for selected naked seed mutants, their original parents and check cultivars. This comparative data indicates that the incorporation of the naked-tufted seed coat trait generally reduces the short fiber count (percentage by weight) in the mutant lines when compared to their original parents.

TABLE 4a

AFIS (Advanced Information System) Data For Some Naked Seed Mutants, Their Original Parents and Check Cultivars.

| | Short Fiber Count (w) | | | | | |
|---|---|---|---|---|---|---|
| Entry | 2006 LBB | 2007 LBB[1] | 2007 LBB[2] | 2007 LBB[3] | 2007 Col. St | Mean |
| | | | % | | | |
| Atlas | 5.8 | 9.6 | 8.2 | 7.6 | 7.3 | 7.7 |
| Atlas-NS-129-2-1-1-1 | 4.9 | 7.1 | 6.9 | 5.8 | 7.4 | 6.4 |
| SC 9023 | 6.2 | 8.9 | 6.5 | 6 | 6.3 | 6.8 |
| SC 9023-NS-57-13-2-1 | 5.0 | 8.7 | 7.0 | 5.9 | 5.6 | 6.4 |
| Tejas | 6.4 | 7.3 | 7.1 | 6.2 | 6.4 | 6.7 |
| Tejas-NS-28-13-3-1-1 | 4.5 | 6.6 | 7.2 | 5.7 | 5.8 | 6.0 |
| FM 989 | 5.1 | 7.3 | — | 5.2 | — | 5.9 |
| FM 958 | 4.8 | 7.4 | 6.5 | 4.6 | 6.2 | 5.9 |
| CV (%) | 11.2 | 7.7 | 12.8 | 23.4 | 9.1 | |
| LSD (0.05) | 0.7 | 1.1 | 1.6 | 2.4 | 1.0 | |

[1] = 2007 Lubbock Naked Seed Nursery
[2] = 2007 Lubbock Elite Lines Nursery
[3] = 2007 Lubbock Hand Ginned Naked Seed Materials Table 4b reveals further AFIS Data for selected naked seed mutants, their original parents and check cultivars. This comparative data indicates that the incorporation of the naked-tufted seed coat trait generally reduces the seed coat neps (count per gram) in the mutant lines when compared to their original parents.

TABLE 4b

AFIS (Advanced Information System) Data For Some Naked Seed Mutants, Their Original Parents and Check Cultivars.

| | Seed Coat Nep (Count) | | | | | |
|---|---|---|---|---|---|---|
| Entry | 2006 LBB | 2007 LBB[1] | 2007 LBB[2] | 2007 LBB[3] | 2007 Col. St | Mean |
| | | | gm | | | |
| Atlas | 25.3 | 9.3 | 5.7 | 26.7 | 12.3 | 15.9 |
| Atlas-NS-129-2-1-1-1 | 11.5 | 9.3 | 5.3 | 12.7 | 7.3 | 9.2 |
| SC 9023 | 26.8 | 10.3 | 17 | 18 | 8.3 | 16.1 |
| SC 9023-NS-57-13-2-1 | 13.1 | 11.3 | 9.7 | 11.3 | 5.0 | 10.1 |
| Tejas | 25.9 | 14 | 9.7 | 12.3 | 9.7 | 14.3 |
| Tejas-NS-28-13-3-1-1 | 11.6 | 5.7 | 12.7 | 8 | 7.0 | 9.0 |
| FM 989 | 18.6 | 6.7 | — | 8.3 | — | 11.2 |
| FM 958 | 21.2 | 5.0 | 7.0 | 15.3 | 5.7 | 10.8 |
| CV (%) | 30.5 | 36.6 | 52.6 | 61.1 | 37.4 | |
| LSD (0.05) | 4.44 | 5.7 | 9.0 | 15.1 | 5.3 | |

[1]= 2007 Lubbock Naked Seed Nursery
[2]= 2007 Lubbock Elite Lines Nursery
[3]= 2007 Lubbock Hand Ginned Naked Seed Materials Table 4c reveals further AFIS Data for selected naked seed mutants, their original parents and check cultivars. This comparative data indicates that the incorporation of the naked-tufted seed coat trait generally maintains the upper quartile length in the mutant lines when compared to their original parents.

TABLE 4c

AFIS (Advanced Information System) Data For Some Naked Seed Mutants, Their Original Parents and Check Cultivars.

| | Upper Quartile Length | | | | | |
|---|---|---|---|---|---|---|
| Entry | 2006 LBB | 2007 LBB[1] | 2007 LBB[2] | 2007 LBB[3] | 2007 Col. St | Mean |
| | | | in | | | |
| Atlas | 1.21 | 1.19 | 1.20 | 1.21 | 1.14 | 1.19 |
| Atlas-NS-129-2-1-1-1 | 1.28 | 1.212 | 1.22 | 1.25 | 1.19 | 1.23 |
| SC 9023 | 1.29 | 1.27 | 1.24 | 1.31 | 1.17 | 1.26 |
| SC 9023-NS-57-13-2-1 | 1.20 | 1.15 | 1.15 | 1.29 | 1.15 | 1.19 |
| Tejas | 1.16 | 1.2 | 1.16 | 1.24 | 1.14 | 1.18 |
| Tejas-NS-28-13-3-1-1 | 1.23 | 1.19 | 1.21 | 1.24 | 1.18 | 1.21 |
| FM 989 | 1.29 | 1.24 | — | 1.29 | — | 1.27 |
| FM 958 | 1.29 | 1.24 | 1.26 | 1.28 | 1.2 | 1.25 |
| CV (%) | 1.8 | 1.9 | 1.1 | 2.6 | 1.8 | |
| LSD (0.05) | 0.02 | 0.04 | 0.02 | 0.06 | 0.04 | |

[1]= 2007 Lubbock Naked Seed Nursery
[2]= 2007 Lubbock Elite Lines Nursery
[3]= 2007 Lubbock Hand Ginned Naked Seed Materials Table 5 states the Pearson Correlation Coefficients for several parameters for selected naked seed mutants including: seed nakedness, percent oil, lint yield, and turnout. This data provides further support for the significance of the trends shown in the above data evidencing an increase in seed oil content, and the maintenance of lint yield and turnout.

TABLE 5

Pearson Correlation Coefficients for Some Parameters for the Naked Seed Entries.
N = 10
Prob > /r/ under Ho: Rho = 0

| | Percent Oil | Lint Yield |
|---|---|---|
| Seed Nakedness | 0.92696 | −0.12867 |
| | 0.0001 | 0.7232 |
| Turnout | −0.73841 | 0.41342 |
| | 0.0148 | 0.001 |

Table 6 shows the yarn quality for ring spun yarn 40Ne for selected naked seed mutants and their original parents. This data supports the commercial quality of the cotton products associated with the mutant lines.

TABLE 6

Yarn Quality for Ring Spun Yarn 40Ne for Some Naked Seed Mutants and Their Original Parents

| Cultivars | Count Strength Product | Elongation | Tenacity | Work | CV | Thin Places | Thick Places | N200 | Hair |
|---|---|---|---|---|---|---|---|---|---|
| Atlas | 2140 | 5.9 | 13.0 | 317.0 | 20.0 | 158 | 958 | 642 | 5.0 |
| Atlas-NS-129-2-1-1-1 | 2228 | 6.1 | 13.9 | 338.5 | 19.2 | 125 | 860 | 526 | 4.5 |
| SC 9023 | 2240 | 6.1 | 13.8 | 340.4 | 18.8 | 101 | 735 | 466 | 4.4 |
| SC 9023-NS-57-13-2-1 | 2312 | 6.3 | 13.8 | 347.2 | 18.0 | 68 | 582 | 375 | 4.3 |
| Tejas | 2192 | 5.9 | 13.7 | 318.2 | 19.3 | 144 | 852 | 535 | 4.5 |
| Tejas-NS-28-13-3-1-1 | 2329 | 6.1 | 14.2 | 338.7 | 18.9 | 109 | 785 | 511 | 4.5 |

The lines carrying the naked seed mutation have reduced seed coat neps, potentially reduced short fiber content, improved yarn quality, and improved AFIS fiber maturity characteristics. Thus, the naked-tufted seed mutant may be critical to the development of ELS (Extra Long Staple) stripper varieties in Texas. It also appears this mutation could significantly reduce both the time and the energy required for ginning, oil extraction, and delinting of cottonseed. The superior fiber quality and improved energy efficiency obtained with the naked-tufted seed mutant will drive its rapid incorporation into new cultivars.

The naked-tufted seed mutant line of *Gossypium hirsutum* L., of the present invention, as developed from lines initially produced by chemical mutagenesis, therefore exhibits significantly reduced formation of linters on the surface of the cotton seed. In general, the lines carrying the naked seed mutation have reduced seed coat neps, reduced short fiber content, improved yarn quality, increased seed oil content, and improved AFIS fiber maturity. In addition, the naked-tufted seed of the mutant line significantly reduces the time and energy required for ginning, oil extraction, and reduces the need to delint the cotton seed prior to planting. Thus the mutant line of the present invention lends itself to incorporation into other well-adapted commercial cultivars of upland cotton to produce additional lines exhibiting the naked-tufted seed coat trait while continuing to produce commercially significant quantities of commercial quality fiber.

Although the present invention has been described in the terms of the foregoing preferred embodiments in conjunction with specific cultivars, plants, seeds, and seed products, this description has been provided by way of explanation only, and is not intended to be construed as a limitation of the invention. Those skilled in the art will recognize additional alternate embodiments of the present invention that might be directed to alternate cultivars, plants, seeds, and seed products. Such alternate choices for specific cultivars, where such are coincidental to the application of the methods, products, and resultant lines, do not necessarily depart from the spirit and scope of the present invention.

REFERENCES

Auld, D. L., E. Bechere, M. D. Ethridge, W. D. Becker, E. Hequet & R. G. Cantrell, 2000. Registration of TTU 202-1107B and TTU 271-2155-C mutant germplasm lines of upland cotton with improved fiber quality. Crop Sci. 40: 1835-1836.

Auld, D. L., M. D. Ethridge, J. K. Dever & P. A. Dotray, 1998. Chemical mutagenesis as a tool in cotton improvement. Proc. Beltwide Cotton Prod. Res. Conf. Memphis, Tenn. Vol. 1: 550-552.

Basal, H. & C. W. Smith, 1997. The association of fiber quality parameters and lint yield components in $F_3$ derived $F_4$ progeny of two upland cotton populations. Proc. Beltwide Cotton Prod. Res. Conf. Memphis, Tenn. Vol. 1: 478-479.

Bowman, D. T., O. L. May & S. D. Calhoun, 1996. Genetic base of upland cotton cultivars released between 1970 and 1990. Crop Sci. 36: 577-581.

Cantrell, R. G. & A. Escabado, 1997. Genetics of fiber strength. Proc. Beltwide Cotton Prod. Res. Conf. Memphis, Tenn. Vol. 2: 1627.

Cotton Incorporated, 2000. Final Report-Fiber Quality. http://www.cottoninc.com.

Gibson, P. T., 1996. Correcting for inbreeding in parent-offspring regression estimate of heritability with non-additive and genotype x environment effects present. Crop Sci. 36: 594-600.

Endrizzi, J. E. and D. T. Ray. 1991. Monosomic and Monotelodisomic Analysis of 34 Mutant Loci in Cotton. Journal of Heredity 82:53-57.

Gaibullaev, I. K. H., M. K. H. Avazkhodzhaev, and A. E. Egamberdiev. 1976. Reaction of Chemomutants of Cotton to Infection by the Pathogen of Verticillium Wilt. Soviet Genetics 11(1); 34-36.

Green, C. C. & T. W. Culp, 1988. The inheritance and relationship of yield and fiber properties and the implications to a cotton breeding program. Proc. Beltwide Cotton Prod. Conf. Memphis, Tenn. Vol. 1: 131.

Hussein, H. A. S., F. A. Al-enani, and M. El-Moghazi. 1982. Histological and Morphological Characteristics of a Glandless Cotton Mutant Induced with Sodium Azide. Eygpt J. Genet. 11:167-173.

Keim, K. R.&J. E. Quisenberry, 1983. Inheritance of fiber quality in a semi-dwarf composite population of cotton (*Gossypium hirsutum* L.) Proc. Beltwide Cotton Prod Res Conf Memphis, Tenn. Vol. 1: 108.

Kloth, R. H, 1998. Analysis of commonality for traits of cotton fiber. J. Cotton Sci. 2: 17-22.

Konoplya, S. P., V. N. Fursov, A. A. Drushkov & G. N. Nuryeva, 1974. Heritability of several quantitative characters in cotton. Soviet Genetics 10: 1462-1464.

Larik, A. S., H. M. I. Hafiz, and Y. A. Al-Saheal. 1983. Azide Mutagenesis in Cotton (*Gossypium hirsutum*). Science and Environment 5: 33-42.

Latimer, S. L., T. P. Wallace & D. S. Calhoun, 1996. Cotton Breeding: High volume instrument versus conventional fiber quality testing. Proc Beltwide Cotton Prod Res Conf Memphis, Tenn. Vol. 3: 1681.

May, O. L.&G. M. Jividen, 1999. Genetic modification of cotton fiber properties as measured by single- and high volume instruments. Crop Sci. 39: 328-333.

Meredith, W. R., Jr, 1984. Quantitative genetics. p. 131-150. n: R. J. Kohel and C. F. Lewis (eds.), Cotton Agronomy Monograph No. 24. ASA, CSSA, and SSSA. Madison, Wis.

Naivar, K. S, 1996. Fiber quality parameters and within-boll yield components of *Gossypium arboreum*. Putative mutant lines. M. S. Thesis. Texas A&M University. 71 p.

Du, X. M., J. J. Pan, R. H. Wang, T. Z H. Zhang, and Y. Zh. Shi. 2001. Genetic Analysis of Presence and Absence of Lint and Fuzz on Cotton. Plant Breeding 120:519

Endrizzi, J. E. and D. T. Ray. 1991. Monosomic and Monotelodisomic Analysis of 34 Mutant Loci in Cotton. Journal of Heredity 82:53-57.

Lee, J. J., O. S. S. Hassan, W. Gao, N. E. Wei, R. J. Kohel, X. Y. Chen, P. Payton, S. H. Sze, D. M. Stelly, and Z. J. Chen. 2006. Developmental and gene expression analyses of a cotton naked seed mutant. Planta 223: 418-432.

Shattuck, V. and F. R. Katterman. Enhanced Unscheduled DNA Synthesis if the Cotyledons of *Gossypium barbadense* L. by Ethyl Methansulfonate (EMS). Biochemical and Biophysical Research Communications 109(3): 1017-1025.

Turley, R. B. and R. H. Kloth. 2002. Identification of a Third Fuzzless Seed Locus in Upland Cotton (*Gossypium hirsutum* L.).

We claim:

1. A mutant cotton seed developed by subjecting an established line of *Gossypium hirsutum*, L. cotton seeds comprising an Atlas-NS-129-2-1-1-1 and/or a SC 9023-NS- 57-13-2-1 cotton seed line to chemical mutagenesis and selectively bred to establish a phenotypic stable mutant cotton seed that exhibits:
  a seed coat trait comprising:
    a first surface area having a predominantly smooth (naked) surface and a second surface area having a tufted quantity of fiber, the first surface area being generally greater than the second surface area, and wherein,
    the mutant cotton seed further comprising the characteristics of:
      reduced linters on the surface of the seed,
      reduced seed coat neps (SCN) on the surface of the seed,
      reduced short length fibers associated with the seed, and
      increased seed oil content when compared to the established line of Gossypium hirsutum L. cotton seeds.

2. A mutant cotton plant developed by subjecting an established line of Gossypium hirsutum L. cotton seeds comprising an Atlas-NS-129-2-1-1-1 and/or a SC 9023-NS-57-13-2-1 cotton seed line to chemical mutagenesis and selectively bred to establish a phenotypic stable mutant cotton seed that exhibits:
  a seed coat trait comprising:
    a first surface area having a predominantly smooth (naked) surface,
    a second surface area having a tufted quantity of fiber,
    the first surface area being generally greater than the second surface area, and wherein,
    the mutant cotton seeds further comprising the characteristics of:
      reduced linters on the surface of the seeds,
      reduced seed coat neps (SCN) on the surface of the seeds,
      reduced short length fibers associated with the seeds, and
      increased seed oil content when compared to the established line of Gossypium hirsutum L. cotton seeds.

3. A mutant Gossypium hirsutum L. seed product developed by subjecting an established line of Gossypium hirsutum L. seeds comprising an Atlas-NS-129-2-1-1-1 and/or a SC 9023-NS-57-13-2-1 cotton seed line to chemical mutagenesis and selectively bred to establish a phenotypic stable mutant cotton seed, wherein the seed product consists of a substantially homogenous assemblage of mutant cotton seeds that exhibit:
  a seed coat trait comprising:
    a first surface area having a predominantly smooth (naked) surface,
    a second surface area having a tufted quantity of fiber,
    the first surface area being generally greater than the second surface area, and wherein,
    the mutant cotton seeds further comprising the characteristics of:
      reduced linters on the surface of the seeds,
      reduced seed coat neps (SCN) on the surface of the seeds,
      reduced short length fibers associated with the seeds, and
      increased seed oil content when compared to the established line of the Atlas-NS-129-2-1-1-1 and/or a SC 9023-NS-57-13-2-1 cotton seed.

4. A mutant Gossypium hirsutum L. plant developed by subjecting an established line of Gossypium hirsutum L. seeds comprising an Atlas-NS-129-2-1-1-1 and/or a SC 9023-NS-57-13-2-1 cotton seed line to chemical mutagenesis and selectively bred to establish a phenotypic stable mutant cotton seed, wherein the mutant plant produces seeds that exhibit:
  a seed coat trait comprising:
    a first surface area having a predominantly smooth (naked) surface,
    a second surface area having a tufted quantity of fiber,
    the first surface area being generally greater than the second surface area, and wherein,
    the produced mutant cotton seeds further comprise the characteristics of:
      reduced linters on the surface of the seeds,
      reduced seed coat neps (SCN) on the surface of the seeds,
      reduced short length fibers associated with the seeds, and
      increased seed oil content when compared to the established line of Gossypium hirsutum L. cotton seeds.

5. A cotton plant according to claim 4.

6. The cotton seed of claim 1, wherein the established line of Gossypium hirsutum L. cotton seeds is an established line selected from a group consisting of Atlas and SC 9023.

7. The cotton plant of claim 2, wherein the established line of Gossypium hirsutum L. cotton seeds is an established line selected from a group consisting of Atlas and SC 9023.

8. The Gossypium hirsutum L. seed product of claim 3, wherein the established line of Gossypium hirsutum L. cotton seeds is an established line selected from a group consisting of Atlas and SC 9023.

9. The cotton line of claim 4, further wherein the established line of Gossypium hirsutum L. cotton seeds is an established line selected from a group consisting of Atlas and SC 9023.

10. A mutant cotton seed developed by subjecting at least one of an Atlas or a SC 9023 line of Gossypium hirsutum L. cotton seeds to ethyl methanesulfonate (EMS) and selectively bred to establish a phenotypic stable mutant cotton seed that exhibits:
  a seed coat trait comprising:
    a first surface area having a predominantly smooth (naked) surface and a second surface area having a tufted quantity of fiber, the first surface area being generally greater than the second surface area, and wherein, the mutant cotton seed further comprising the characteristics of:
  reduced linters on the surface of the seed,
    reduced seed coat neps (SCN) on the surface of the seed,
    reduced short length fibers associated with the seed, and
    increased seed oil content when compared to the corresponding parent Atlas or SC 9023 line of Gossypiumhirsutum L. cotton seeds.

* * * * *

UNITED STATES PATENT AND TRADEMARK OFFICE
CERTIFICATE OF CORRECTION

| | |
|---|---|
| PATENT NO. | : 9,877,445 B2 |
| APPLICATION NO. | : 12/197296 |
| DATED | : January 30, 2018 |
| INVENTOR(S) | : Dick L. Auld and Efrem Bechere |

It is certified that error appears in the above-identified patent and that said Letters Patent is hereby corrected as shown below:

In the Specification

On Column 1, Line 15, before the "FIELD OF THE INVENTION" please insert the following paragraph:
-- STATEMENT OF FEDERALLY FUNDED RESEARCH
This invention was made with government support under 2005-38868-02376 awarded by the United States Department of Agriculture/National Institute of Food and Agriculture. The Government therefore has certain rights in the invention. --

Signed and Sealed this
Eighth Day of February, 2022

Drew Hirshfeld
*Performing the Functions and Duties of the
Under Secretary of Commerce for Intellectual Property and
Director of the United States Patent and Trademark Office*